US006287307B1

(12) United States Patent
Abboudi

(10) Patent No.: US 6,287,307 B1
(45) Date of Patent: Sep. 11, 2001

(54) APPARATUS AND METHODS FOR CLAMPING SPLIT BONE SECTIONS

(76) Inventor: Shalom Y. Abboudi, 126 N. 9th Ave., Highland Park, NJ (US) 08904

( * ) Notice: Subject to any disclaimer, the term of this patent is extended or adjusted under 35 U.S.C. 154(b) by 0 days.

(21) Appl. No.: 09/628,487

(22) Filed: Jul. 31, 2000

(51) Int. Cl.[7] .................................................. A61B 17/56
(52) U.S. Cl. ............................ 606/54; 606/57; 606/69; 606/71; 606/105
(58) Field of Search .................................. 606/57, 59, 54, 606/55, 56, 58, 60, 105, 71, 69, 103, 205–208

(56) References Cited

U.S. PATENT DOCUMENTS

| | | | |
|---|---|---|---|
| 3,960,147 | * | 6/1976 | Murray .................................... 606/54 |
| 4,275,490 | * | 6/1981 | Bivins .................................... 27/21.1 |
| 4,790,303 | * | 12/1988 | Steffee .................................... 606/54 |
| 5,053,039 | * | 10/1991 | Hofmann et al. ....................... 606/87 |
| 5,649,925 | * | 7/1997 | Barbera Aleacreu ................ 606/103 |
| 5,849,012 | * | 12/1998 | Abboudi ................................. 606/57 |
| 6,045,551 | * | 4/2000 | Bonuti .................................... 606/60 |
| 6,096,079 | * | 8/2000 | Eaton ..................................... 606/54 |

\* cited by examiner

Primary Examiner—Pedro Philogene

(74) Attorney, Agent, or Firm—Henry I Schanzer

(57) ABSTRACT

A clamping assembly for clamping together first and second sections of bone having, when so clamped, a common external surface generally perpendicular to contacting surfaces of the first and second bone sections, and each bone section having a side surface generally parallel to the common external surface and transversely joined to the common external surface. The clamping assembly includes first and second plates, each plate having a horizontal section and a vertical section. The first and second plates are aligned and disposed opposite each other with the horizontal section of the first plate being disposed along the common surface of the first bone section and its vertical section disposed along the side surface of the first bone section and the horizontal section of the second plate being disposed along the common surface of the second bone section and its vertical section disposed along the side surface of the second bone section. The horizontal section of each plate is grooved to enable a wire to pass through the groove of the plates and to be wound in a figure of eight configuration for pulling the plates toward each other and for compressing the two bone sections together without the figure-of-8 wire touching the bone section. In one embodiment, an oblique hole is formed in the vertical portions of the plates to enable a second wire to pass underneath the bone sections and through the oblique holes to allow a circumferential wire to pass around the plate so as to also provide a holding and compressive force for the two bone sections.

23 Claims, 8 Drawing Sheets

APPARATUS AND METHODS FOR CLAMPING SPLIT BONE SECTIONS

BACKGROUND OF THE INVENTION

This invention relates to surgical devices and, in particular, to clamping and fixation assemblies for holding together split sections of bones.

In U.S. Pat. No. 5,849,012, titled "Surgical Clamping Assemblies and Methods of Use", issued to the present Applicant and the teachings of which are incorporated herein by reference, applicant identified a problem existing in the art pertaining to the use of wires for sternal fixation. That is, in the prior art a wire is used to directly clamp two bone halves together. The wire may cut right through the bone causing damage to the bone rather than the expected healing. In U.S. Pat. No. 5,849,012, Applicant taught the use of clamping assemblies to be mounted on separate sections of bones and the use of wire to interconnect the clamping assemblies without the wire touching the bone area underlying the clamping assembly. Thus the wire does not cause the cutting of the bony sections being clamped. In refining his prior work, Applicant recognized the need for a clamping assembly which would have a relatively low profile (i.e., be relatively thin) and where the clamping assembly avoids the use of hooks or parts extending outwards from the bone sections, in order to reduce any outward pressure (i.e., push out) against the flesh and skin layer(s) overlying the bone sections. By way of example, it is desirable that a clamping assembly for clamping sternal halves be easy to mount securely on the bone sections and have a low profile while still providing rigid and dynamic fixation.

SUMMARY OF THE INVENTION

Apparatus embodying the invention includes a clamping assembly for clamping together first and second sections of bone having, when so clamped, a common external surface generally perpendicular to contacting surfaces of the first and second bone sections, and each bone section having a side surface generally parallel to said contacting surface and transversely joined to said common external surface. The clamping assembly includes first and second "L-shaped" plates; the horizontal portion of the "L" having a top surface and a bottom surface with a groove therebetween for enabling a wire to pass through the groove between the top and bottom surfaces. The first and second plates are generally aligned opposite each other, with the first plate being secured to the first bone section and the second plate being secured to the second bone section and, as to each plate, the horizontal portion of its "L" section resting on the common external surface and the vertical portion of its "L" section abutting its respective side surface. A wire is disposed within at least a portion of the groove and is wound between the first and second plates in a figure-of-eight configuration for pulling the two plates toward each other and simultaneously compressing the two bone sections together without the wire touching the bone surface underneath the plate and without the wire extending above the top surface of the plates.

In a particular embodiment, as to each plate, the horizontal portion of the "L" is made generally of triangular shape to enable the figure-of-eight configuration to be formed without sharp bends. Also, as to each plate, the base of the triangle defines its rear section and the apex of the triangle defines its front section.

In still another embodiment of the invention, as to each plate, a spike extends from the generally middle region of the vertical section of the "L" for securing the plate to its associated bone section.

In a particular embodiment, as to each plate, an oblique hole is formed in the vertical portion of the "L" distal from the horizontal section and a notch is formed in the back of the base of the triangle to enable a circumferential wire to be passed underneath the bone sections, through the oblique holes and around the bone sections via the notch in each base for securing the bone sections together.

A method of clamping two bone sections together includes passing the circumferential wire through and around the first and second plates to provide a first level of compression and then positioning a wire within at least a portion of the groove and winding it in a figure-of-eight configuration between the first and second plates for pulling the two plates toward each other and simultaneously compressing the two bone sections.

In accordance with another aspect of the invention there is provided a plate driver for holding the plates in an aligned relationship and for then driving the plates from the back of the vertical "L" section of the plates into respective bone sections whereby the plates retain their alignment and the spikes are easily and securely inserted into their respective bone sections.

BRIEF DESCRIPTION OF THE DRAWINGS

In the accompanying drawings like reference characters denote like components.

DETAILED DESCRIPTION OF THE INVENTION

Figure 1:
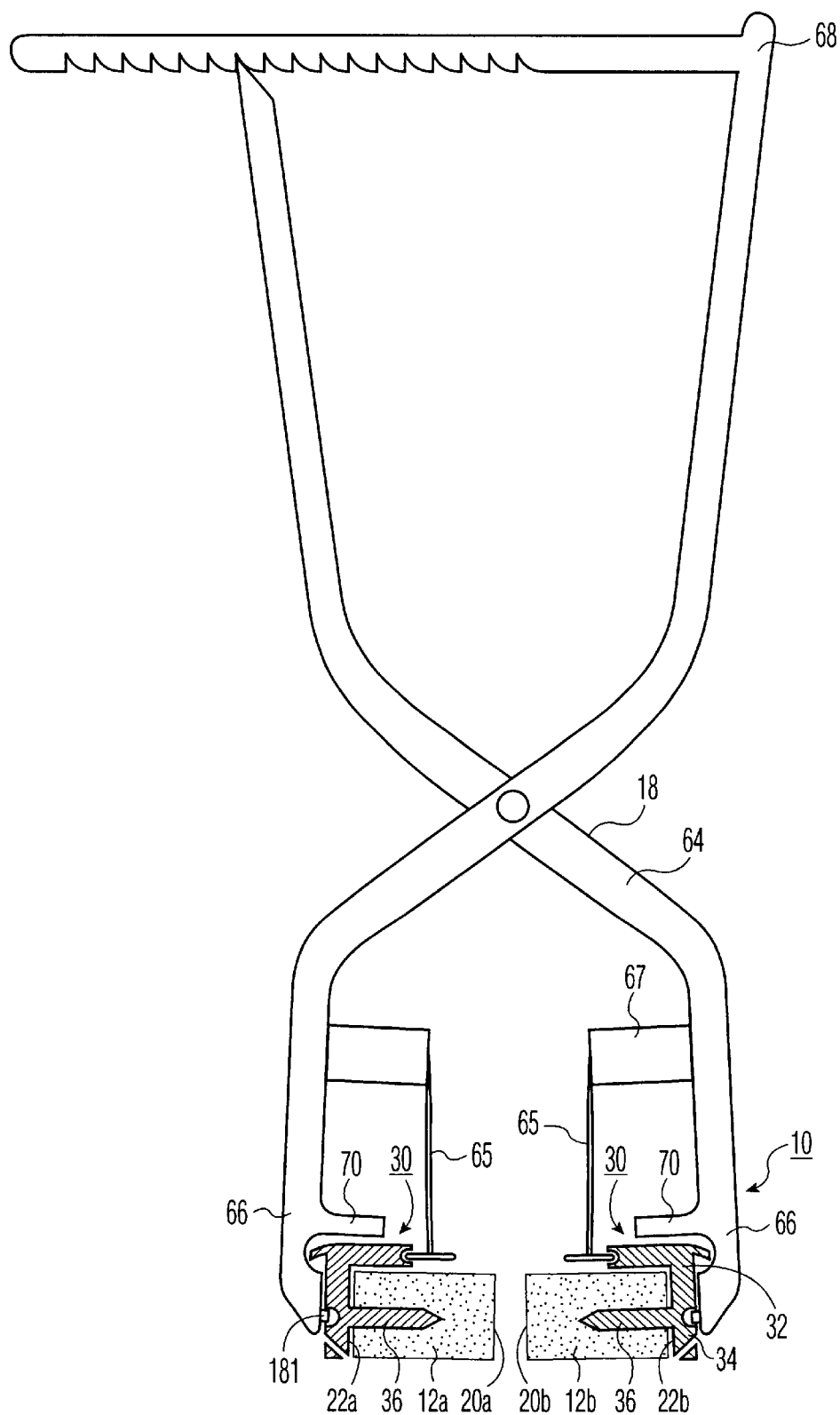
FIG. 1 is a cross section of an assembled clamping assembly in accordance with this invention and further illustrating how the assembly is applied and secured to a pair of sternal halves being compressed together.
Figure 2:
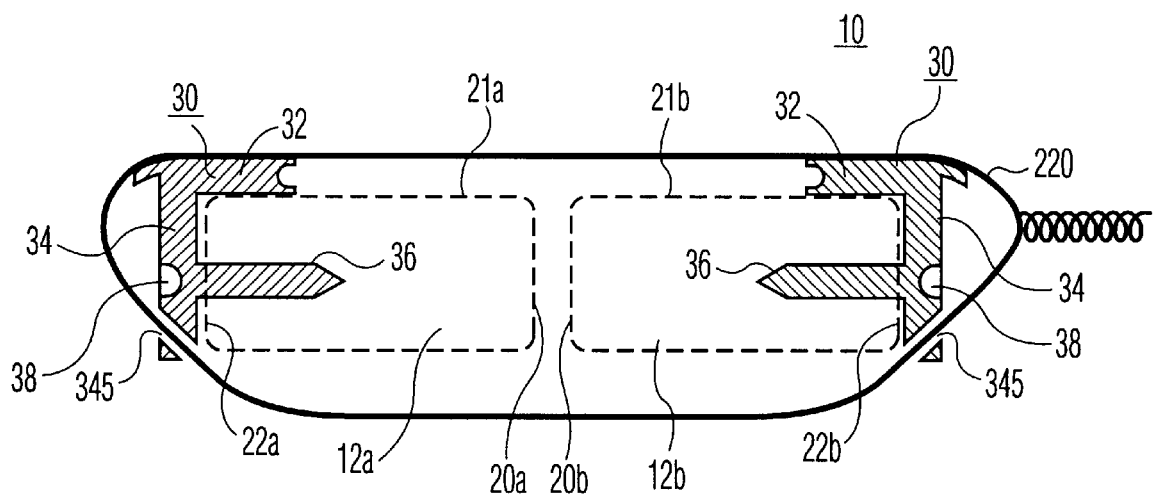
FIG. 2 is a cross-section of two clamps embodying the invention secured to respective sternal halves with a circumferential wire, in accordance with the invention.

For ease of the discussion to follow refer to FIGS. 1 and 2 and note that the invention is directed to a clamping assembly 10 for clamping together two sections (12a, 12b) of bones which are to be clamped and compressed together so they can heal into a single unit. In the description to follow and in the appended claims, the following apply. The two bone sections (12a, 12b) have contacting surfaces (20a, 20b). The two bone sections (12a, 12b) have (or define) a common top (external) surface (21a, 21b) generally perpendicular to their contacting surfaces (20a, 20b). Each bone section has a side surface (22a, 22b) generally parallel to the contacting surfaces and transversely joined to the common surface (21a,21b). The clamping assembly of the invention may be used in conjunction with the repair of any relatively flat bone which is split. However, in the discussion to follow the invention is illustrated for fixation of the sternum following median sternotomy (where the sternum is split longitudinally) as is commonly the case in open heart surgery.

A clamping assembly 10, in accordance with this invention, ideal for fixing flat bones such as the sternum, is shown in FIG. 1. FIG. 1 shows the assembly fully in place for clamping together the two sections, 12a and 12b, of a sternum which had been previously split (e.g., sawed) along the extending length of the bone, as is commonly performed in open heart surgery. FIG. 1 shows a cross section of the sternum which is elongated in a direction perpendicular to the plane of the drawing.

As illustrated in FIG. 1, a compression means, plate driver 18, is still in place in the process of compressing the two sternal halves against one another. For ease of illustration, the two contacting surfaces 20a, 20b of the sternal halves which are being compressed together are shown spaced apart. However, in the condition being illustrated, the two contacting surfaces will actually (and eventually) be tightly compressed against each other.

The clamping assembly 10 includes two identical sternal plates 30. An expanded cross-sectional view of a clamp assembly 10 is shown in FIG. 2. Each sternal plate 30 comprises generally flat top portion, 32 of a rigid material, e.g., stainless steel, ceramic or plastic, mounted and attached to a side bar ("post") 34 with a spike 36 extending from the mid-region of the side bar. Thus, each sternal plate is generally F shaped as shown in FIGS. 1, 2 and 4–6.

Figure 3:
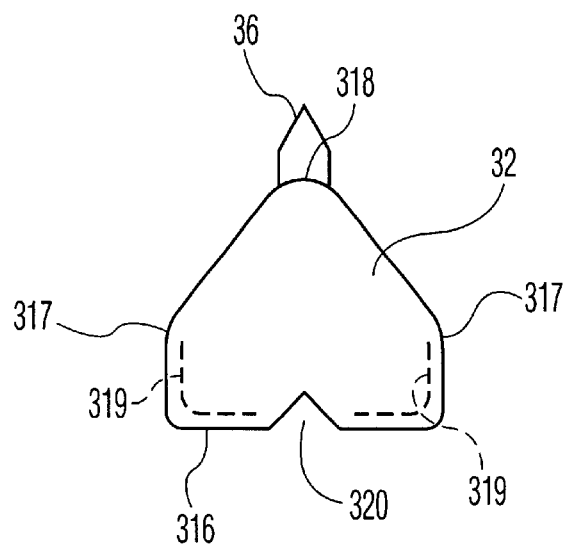
FIG. 3 is a top view of a sternal plate embodying the invention showing a notch formed in the rear section of the flat top portion of the plate.
Figure 4:
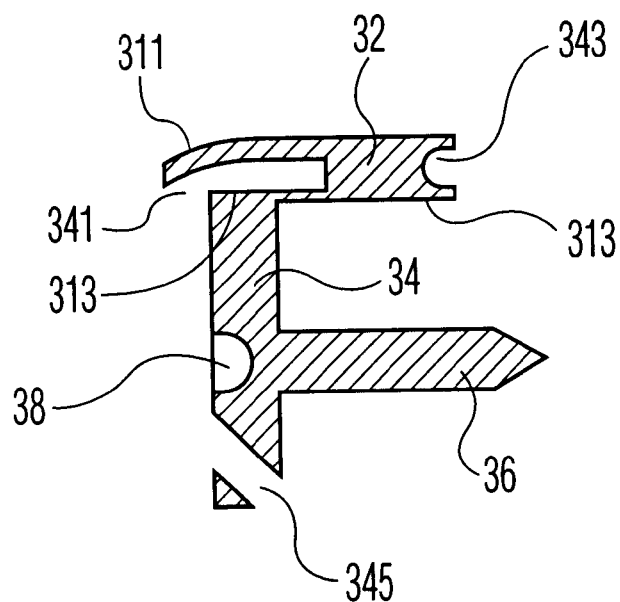
FIGS. 4–6 are different views of a sternal plate embodying the invention showing grooves in the front and back regions of the top plate, a side post extending from the rear section of the flat top section, a "dimple" along the side post and an oblique hole in the bottom of the post.
Figure 5:
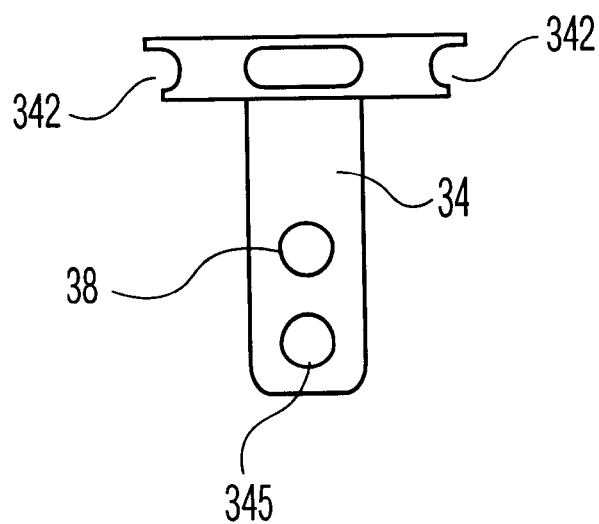
Figure 6:
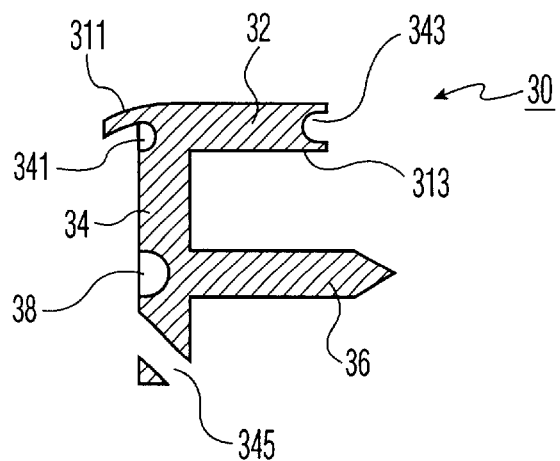

Alternatively, each sternal plate may be characterized as an inverted "L" with a spike extending from the vertical portion of the L. The horizontal portion of the "L" shaped plate corresponds to the flat top section 32 of plate 30 and may be of a generally triangular shape (see FIG. 3) having a bottom surface which is intended to be placed, and rest, on top of the common surface 21a, 21b ( i.e., the top "external" portion of the bone section 12a, 12b). The triangular flat top (horizontal) portion 32 has a base, or rear portion, 316 and an apex, or front section 318 (see FIG. 3). In the center of the back region 316 there is a (inverted) V-notch 320. The V-notch 320 functions to guide and keep a "circumferential" wire 220 (shown in FIG. 2) centered and between the sides of the plate 32. In FIG. 3, dashed lines 319 on either side of the rear section are drawn to indicate that there is a groove extending around the back (341 in FIG. 4) and the rear sides (342 in FIG. 5) of the triangularly shaped flat top section. This groove (341 in FIG. 4 and 342 in FIG. 5) is to ensure that a wire can be passed between the top and bottom surfaces of the flat top (horizontal) section 32 without having to contact the underlying bony section. The triangular shape of the top section is to facilitate the winding of a wire about a pair of plates 30 in figure-of-8 configuration without requiring any sharp bends.

The triangular top plate section 32 of plate 30 is supported by a "side" post 34 which is also called the "side bar" since it is designed and intended to abut the side surface 22a, 22b of the bone sections. The post 34, also referred to as the vertical section of the "L" shaped plate, extends from the bottom side of region 32 for a distance which is somewhat greater than the thickness of the side surfaces 22a, 22b of the bone sections against which the post 34 is to be pressed. Approximately midway between the top and bottom of the post 34 there is a spike 36 which extends in a direction generally parallel to the horizontal section 32 of the plate. In the embodiment shown in FIGS. 1–6, the spike extends beyond the front edge 318 of the top plate section 32. Opposite the spike, on the back side of post 34, there is a circular recessed area ("dimple") 38 which functions as a location and holding spot for the plate driver 18 to drive the spike 36 into a bone section, as further discussed below.

Figure 7:
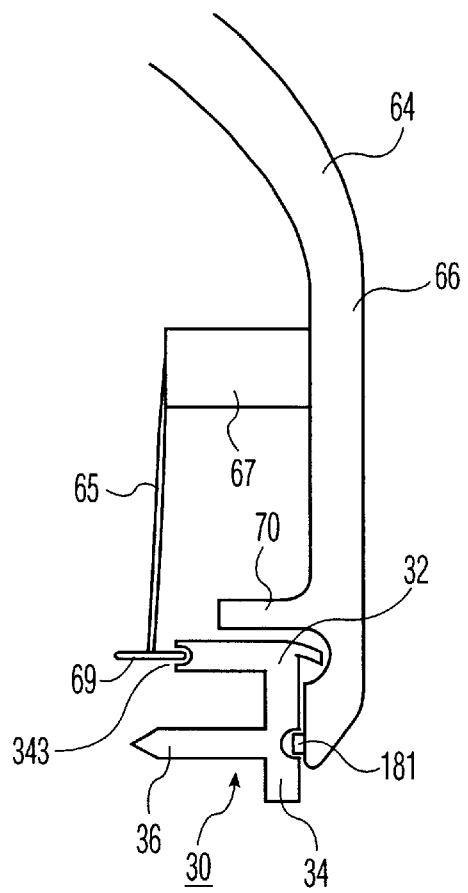
FIG. 7 is a more detailed view of the section of FIG. 1 pertaining to the tool holding a plate.

Certain other features of the sternal plate 30 are as follows. The top (horizontal) plate section 32 has a top surface 311 and a bottom surface 313. The thickness of the horizontal plate 32 is sufficient to form a groove between the top and bottom plates to enable a connecting figure-of-8 wire to pass through the groove. In the rear portion of the top plate, between the top and bottom surfaces there is formed a recessed portion 341 to guide and hold the interconnecting figure-of-8 wire 120 (see FIG. 8B) in place. Groove 341 ensures that a wire 120 may be placed or passed between the top and the bottom of the flat top section, as further discussed below. The triangular shape of the horizontal plate 32 helps in the forming of a figure-of-8 configuration with wire 120, also as discussed below. The top horizontal section 32 of the plate also has a groove 343 along its front 318. Groove 343 functions to aid the plate driver 18 to hold the plate in place (see FIGS. 1 and 7) when the driver inserts the spike into a bone section. The top horizontal plate section also includes a groove 342 running along the sides of the plate. The side groove need not extend the full length of the sides of the triangle and in one embodiment, as shown by line 319 in FIG. 3, extends from the back (base of the triangle) 316 to a point 317 along the sides of the top flat (horizontal) section. The grooves 341 and 342 function to guide the interconnecting figure-of-8 wire 120 and to ensure that the wire is kept above the common bone surface 21a, 21b. The triangular top section is generally flat. However, there is a curving down of the top section near the rear region 320 to provide a smoother transition and to make it less prominent under the skin and avoid irritation of the tissue in the area.

There is an oblique hole 345 formed in the bottom portion of post 34 (the vertical portion of the "L"). The oblique hole enables the threading and passage of a circumferential wire 220 between the pair of plates forming a clamping assembly as shown in FIG. 2.

As shown in FIGS. 1 and 2, the two clamps 30 face towards each other and it is convenient to refer to the base or rear 316, or to the apex or front 318 portions of the clamps 30. Each spike 36 is an integral extension of its plate and is of the same material as its plate and terminates in a pointed spike 36 for penetration into the sternal bone, as shown. Also, as shown, in this embodiment the spike extends (a short distance) beyond the front point 318 of the top section 32 of the plate. However, the spike could in fact be shorter than the flat top section. The spike 36 of each sternal plate functions to secure its plate 30 to its respective bone section.

Figure 8A:
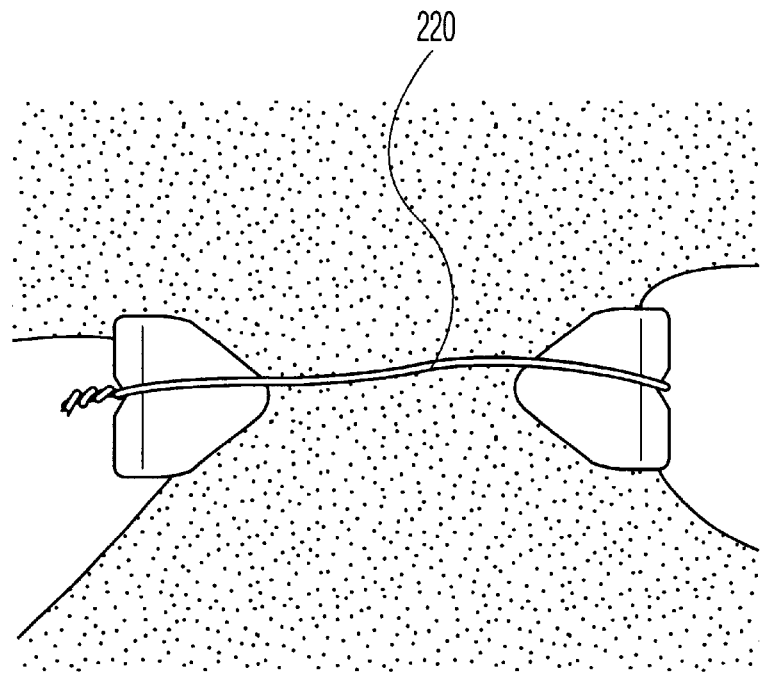
FIGS. 8A and 8B are top views of different wire fixations in accordance with the invention.
Figure 8B:
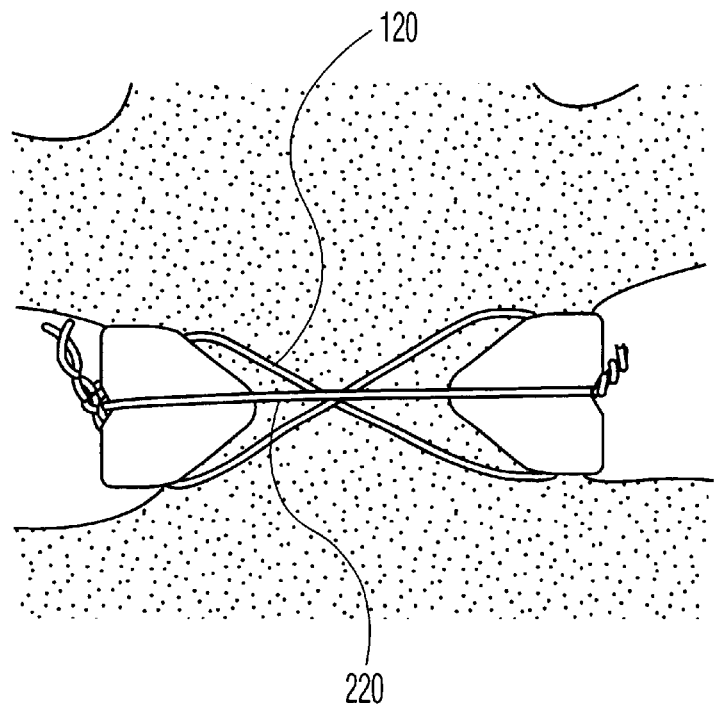

The clamping assembly includes a "circumferential" wire 220, as shown in FIGS. 2, and 8A and an interconnecting figure-of-eight wire 120 (as shown in FIG. 8B) which is tightly wrapped around the outer periphery of the top plate sections 32, and within the back grooves 341 and side grooves 342 of top section 32, in a figure-eight configuration for maintaining the clamps 30 in tightly clamped relationship with the sternal halves 12a, 12b.

A feature of the invention is that each pair of sternal plates 30 is mounted on a respective sternal half, with each plate 30 facing the other. Note, that while the two plates 30 are carefully aligned with one another, neither plate extends over both sternal sections and neither plate directly spans the contacting surfaces 20a, 20b of the sternal sections. An advantage of this is that the fit of each plate with its respective sternal half is independent of any surface irregularities of the two sternal halves relative to one another. Specifically, the two clamps on opposite sides of the contacting surfaces 20a, 20b need not be co-planar, thereby enabling each clamp to be securely fastened to its respective sternal half, regardless of variations from coplanarity of the sternal upper surfaces. Moreover, the flat top, horizontal, portions 32 do not touch each other to allow for full compression of the bone ends (contacting surfaces 20a, 20b). The clamps 30 are made large enough and of sufficient sturdy materials to withstand the applied compressive stresses. The clamps can be formed of steel or any known rigid ceramic or plastic.

With a pair of sternal plates 30 mounted in aligned relationship on respective sternal halves as shown in FIGS. 1 and 2, the mechanical compression applying means (plate driver 18) is used for tightly pressing the plates against their respective sternal sections and the sternal sections against one another. Different compression applying means can be used, but owing to surface irregularities of the split sternum, it is desirable to apply the compressive forces to the "back" portion of the sternal plates 30 for causing the spikes 36 to be driven into their respective bone sections. To this end, the aforementioned recess hole (dimple) 38 in back of post 34 is provided in each sternal plate 30 to enable each plate 30 to be securely engaged with the plate driver 18. In FIG. 1, the plate driver jaws 64 are disposed vertically relative to the clamping assembly. It should also be appreciated that the ends 66 of the plate driver 18 are applied to the back sides of posts 34 supporting plates 32. As shown in FIGS., 7, 7B and 7C, the end 66 includes a projecting piece 181 which fits into the "dimple" 38 and is used to press the spike 36 into a bone section. It should be appreciated that a plate driver (as shown in FIG. 7C) may be used, without a sternal plate being loaded in it, to compress the two sternal halves. Thus, the plate driver may be used to align the sternal plates to each other and to secure them to respective sternal halves and to also hold the sternal halves together prior to the plates being applied or after the plates are applied while the two sternal halves are being tied together. Clamping assemblies are used, as described, at spaced apart intervals along the elongated sternum (not shown) for firmly securing the two sections together.

In FIG. 1, plate driver 18 is shown comprising a pair of jaws 64 having ends 66 which, in conjunction with extensions 70, are dimensioned to fit on top of and around the sternal plates 30. As detailed in FIGS. 7, 7A, 7B and 7C, plate driver 18 includes rotatable arms 65 dependent from projection 67, where arms 65 function as "plate suspenders". The arms 65 terminate in an inverted T-shape, with the bottom part of the "T" forming an extension 69 designed to fit into a "front" groove 343 formed in the front (apex) 318 of the horizontal plate section 32 for providing firm engagement between the plate driver 18 and the sternal plates 30. The plates 30 are loaded onto the plate driver 18 by retracting (raising) the arms 65, then placing the plates 30 under projections 70 and then lowering the arms 65 to enable extensions 69 to engage the plates 30 and hold the plates 30 in place. The arms 65 thus function to hold the sternal plates securely. Then, upon squeezing the handles of the plate driver, the spikes 36 mounted on sternal clamps 30 are driven into their respective bone sections while the two sternal sections are also being pushed against each other.

The plate driver 18 may be used to hold a pair of sternal plates 30 and to align them on opposite sides of a split bone section. As illustrated in FIG. 1, a simple ratchet mechanism 68 is used for applying a selected level of compressive force.

After using the plate driver 18 to place and align the sternal plates 30 on their respective bone sections and to drive the spikes 36 into their respective bone sections, the plate driver may be removed and the two sternal plates (clamps) 30 may be firmly secured together for maintaining the compressive force. The securing process may be accomplished by use of one or more of the following:
   a) One wire closure which may include the use of a circumferential wire 220 as shown in FIGS. 2 and 8A;
   b) Another wire closure may include a figure-of-8 interconnecting wire 120 wrapped around the two top sections 32 of the plates in the shape of a figure-8, as shown in FIG. 8B; and
   c) Still another wire closure includes a rectangular-like interconnecting wire 122 going around the outer periphery of the two top sections 32 of the sternal plates.

As shown in FIG. 2, the circumferential wire 220 is passed below the bone sections and then threaded through the oblique holes 345 in the bottom sections of the posts 34. The wire 220 is then raised up and passed through the V-notch 320 in the base of the triangular plate and then tightened.

The figure-of-8 interconnecting wire 120 is wound around the two top sections 32 of plates 30. The wire 120 is passed through the recess (groove) 341 formed in the rear portion of the section 32 and/or through grooves 342 formed along the sides of plate top 32. The grooves 341 and/or 342 ensure that the wire 120 is securely nested between the top and bottom surfaces of the top flat section 32 and ensures that the wire will not slip. The triangular shape of the top plate makes it easier for wire 120 to be wound between the two plates in a figure-8 configuration, without any sharp bends.

In accordance with the clamp assemblies embodying the invention, securing wires 120 (see FIG. 8B) which extend between the two plates are not engaged with any of the surfaces of the sternal halves so as to cut into the surfaces. Furthermore, the figure-of-8 wire, 120, generally lies above the common surface 21a, 21b and will generally be slightly spaced above the bone surfaces. Accordingly, in those situations where it is necessary to re-enter the chest cavity and particularly in an emergency situation, the clamping assemblies 10 can be easily and quickly removed by cutting through the wrapping wire.

The figure-of-8 configuration produces selective compression of the external surfaces of the sternum. When a "distractive" force is applied, such as when breathing, the fixation construct holds the external surface rigidly in place, resulting in compression of the inner (i.e., contacting) surfaces of the bone. This results in what is commonly known as the tension band repair.

If the figure-of-8 wire 120 is used in conjunction with circumferential wire 220, then wire 220 would typically first be installed and tightened. Then, the interconnecting figure-of-8 wire 120 is passed on the outside of the circumferential wire 220, as shown in FIG. 8B. The wires 120 and 220 are typically secured by twisting the ends of the wires around one another. The twisted ends of the wires may then be placed along the sides of the plates, as shown in FIGS. 8A and 8B.

The use of wires 120 and 220 would constitute a two-wire fixation and would be as shown in FIG. 8-B. If desired, a three-wire fixation can be employed by winding a wire 122 in a rectangular fashion around the back of the plates 32.

Figure 9:
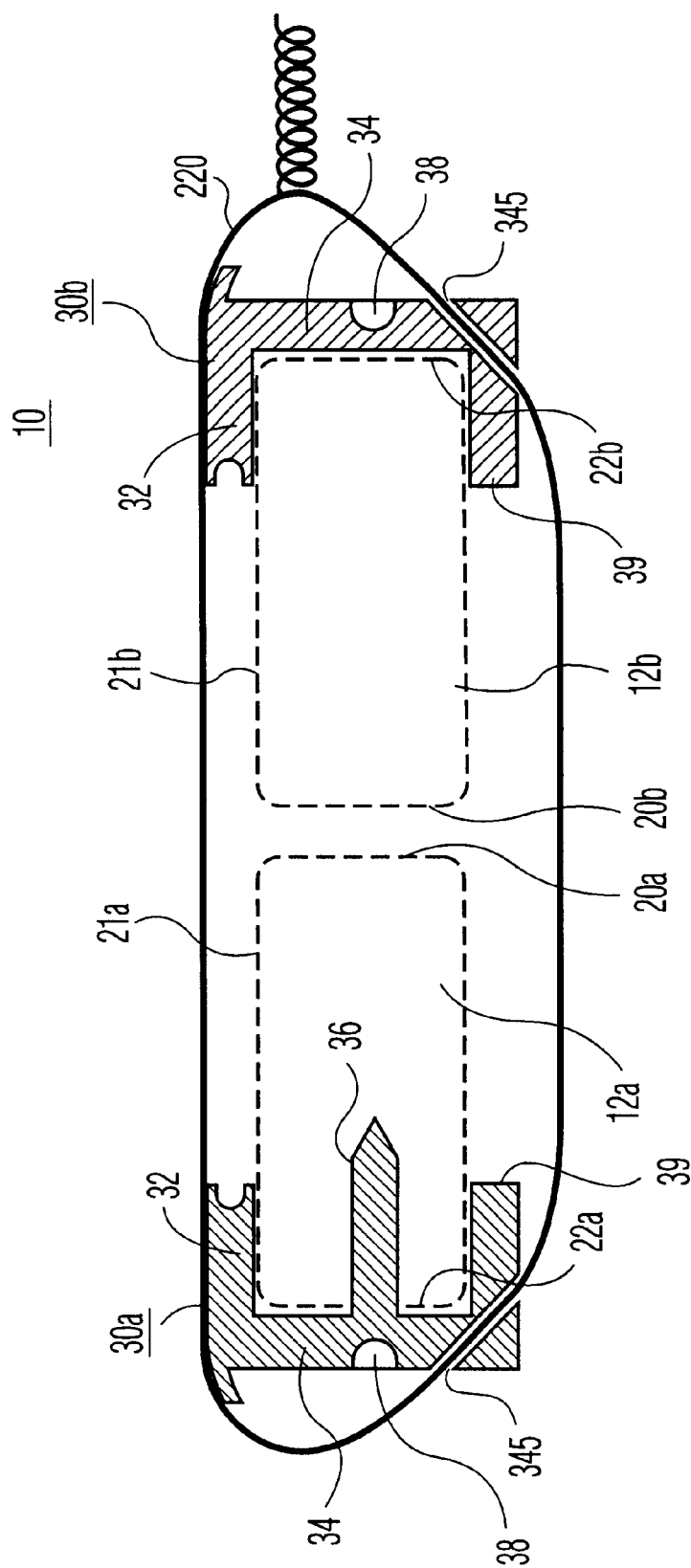
FIG. 9 is a cross-section of two other clamps embodying the invention secured to respective sternal halves with a circumferential wire, in accordance with the invention.

In the discussion above, a spike has been used to secure a plate to its respective bone section. However, as shown in FIG. 9, it should be appreciated that a c-type clamp in the form shown as 30a or 30b may be used instead of the plate 30. Clamp 30a is like plate 30 except that a fiat bottom section 39 is added to the base of post 34. Clamp 30b is like clamp 30a except that the spike 36 has been eliminated. The flat bottom section 39 may be used instead of the spike 36 to secure the plate 30b to its respective bone section. As above each plate 30a and/or 30b would be aligned and inserted into, or around, its respective bone section by a plate driver meshing with locator hole 38 and pushing against the back of the plate. The bottom horizontal plate 39 may be an integral part of the vertical post 34 connected to horizontal plate 32 and the oblique hole 345 is extended through the bottom plate to enable the circumferential wire 220 to be passed through and tightened to hold and compress the bone section 12a and 12b together.

Figure 7A:
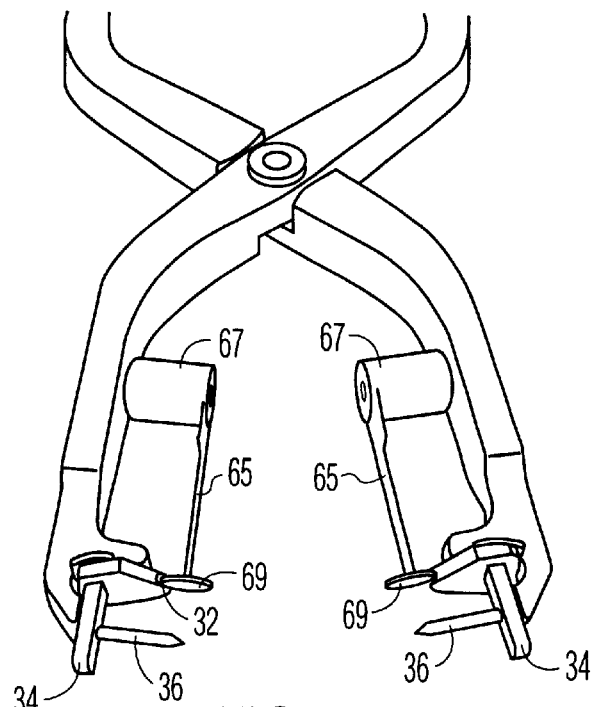
FIGS. 7A, 7B and 7C are various views of a plate driver with and without plates mounted thereon.
Figure 7B:
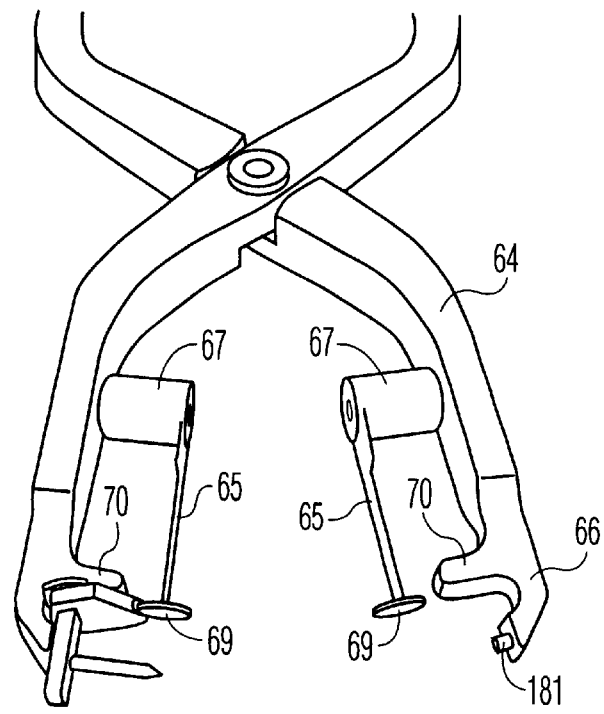
Figure 7C:
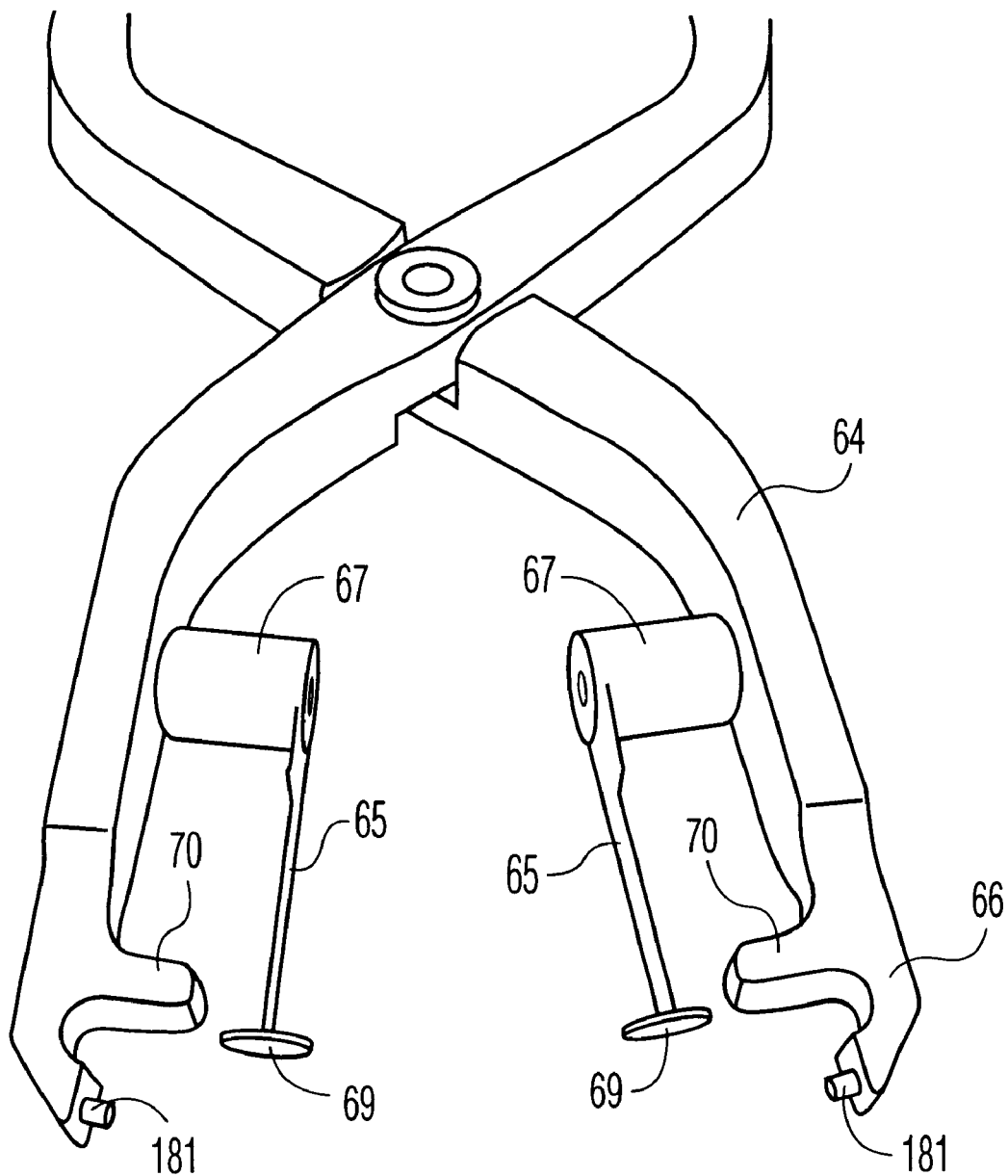

A particular method for clamping a split bone in accordance with the invention may include the following steps:

1—Load a pair of sternal plates 30 onto the plate driver as shown in FIGS. 1 and 7A.

2—Pass a section of circumferential wire 220 underneath the bone sections 12a, 12b.

3—Pass wire 220 through the oblique holes 345 in posts 34 of the sternal plates abutting sections 22a, 22b, as shown in FIG. 2.

4—After the wire is "threaded" through the oblique holes 345, the plate driver 18 is used to mount the sternal plate onto the external surface of the bone section and to insert and secure the plates to the bone sections.

5—The driver 18 may be used to "reduce" the sternal bone halves and align the top section 32 of each plate along the common surface 21a, 21b.

6—The plate driver is gently squeezed to insert the sternal plate on either side of surfaces 22a, 22b of the bone sections 12a, 12b.

7—Another plate driver or a plate holder (not shown) may be used to hold the sternal plates in place and to hold the bones firmly in place. Then the plate driver is removed and a surgeon can work with the circumferential wire.

8—The ends of the circumferential wire 220 are then wound through the v-notch, tightened, twisted and cut back.

9—A wire 120 is then passed around the back of the two plates through the side grooves provided for its passage and then wound in a figure-of-eight configuration.

In the discussion above, reference has been made to the use of wire to interconnect the plates. However, it should be understood that a thread, a nylon cord or its equivalent may be used.

What is claimed is:

1. A clamping assembly for clamping together first and second sections of a relatively flat bone cut along a line generally transverse to the two sections comprising:

first and second plates;

means for securing the first plate to a first bone section on one side of said line and means for securing the second plate to a second bone section opposite to said first plate on the other side of said cut line;

said first and second plates being set back from said cut line and generally aligned opposite each other;

each one of said first and second plates having a relatively flat top portion, said flat top portion having a top surface and a bottom surface, with a groove formed between the top and the bottom surfaces for enabling a wire to be passed through the groove, the bottom surface of each plate for disposition on the top surface of its corresponding bone section; each plate having a front section and a rear section, the front section of each plate for facing said cut line and the front section of the other plate;

a wire; and means for positioning the wire within at least a portion of said groove and for winding the wire between the first and second plates for pulling the two plates toward each other and simultaneously compressing the two bone sections together without the wire touching the bone surface underneath the plate and without the wire extending above the top surface of the plates.

2. A clamping assembly as claimed in claim 1, wherein the plates are triangular in shape with the rear section being the base and the front section being the apex of the triangular shape.

3. A clamping assembly as claimed in claim 1, wherein each plate, at its rear section, includes a post extending from the bottom surface of the rear section; and wherein said means for securing the first plate to a first bone section and the second plate to a second bone section includes, for each plate, a spike formed midway along the post, extending from said post in a direction generally parallel to the plate from the rear to and beyond the front section of the plate.

4. A clamping assembly as claimed in claim 3, wherein each one of said posts extends in a direction generally parallel to outer side surface of its associated bone section for a length approximately equal to the thickness of the bone section, and wherein said post includes an obliquely formed hole in the bottom portion of the post.

5. A clamping assembly as claimed in 4 wherein a circumferential wire is passed underneath the bone section and through the obliquely formed holes in the posts associated with the first and second plates.

6. A clamping assembly as claimed in claim 4, wherein each plate includes a recessed pressure point on the outside of the post, that is the side opposite to the one in which the spike is mounted, for enabling compression means to be applied to that pressure point to push the spike into its associated bone section.

7. A clamping assembly as claimed in claim 2, wherein a groove is formed along a portion of the sides of each plate for enabling a wire to pass through the groove.

8. A clamping assembly as claimed in claim 2, wherein a groove is formed in the front section of each plate for enabling a tool to hold the plates.

9. A clamping assembly as claimed in claim 1, further including a tool for holding the fist and second plates, said tool for securing the plates to respective first and second bone sections so that the first and second plates are in general alignment with each other.

10. A clamping assembly as claimed in claim in claim 9, wherein the tool for holding the first and second plates also includes means for driving the spike into its respective bone section.

11. A clamping assembly as claimed in claim 1, wherein each plate is generally C-shaped, with a generally flat top portion, a vertical portion and a generally flat bottom portion and, as to each plate, the top flat portion is for being disposed along the top of a bone section, the vertical portion is for being disposed along the outer side surface of a bone section, and the bottom flat portion is for being disposed underneath the corresponding bone section.

12. A clamping assembly for clamping together first and second sections of bone having, when so clamped, a common external surface generally perpendicular to contacting surfaces of the first and second bone sections, and each bone section having a side surface generally parallel to said contacting surfaces and transversely joined to said common external surface, the clamping assembly comprising:

first and second "L"-shaped plates; the horizontal portion of the "L" having a top surface and a bottom surface with a groove therebetween for enabling a first wire to pass through the groove between the top and bottom surfaces;

means for disposing the first and second plates in a general alignment opposite each other and securing the first plate to the first bone section and the second plate to the second bone section, with the horizontal portion of the "L" resting on the common external surface and the vertical portion of the "L" abutting the corresponding side surface of the bone section; and means for positioning a first wire within at least a portion of said groove and for winding the wire between the first and second plates for pulling the two plates toward each other and simultaneously compressing the two bone sections together without the wire touching the bone surface underneath the plate and without the wire extending above the top surface of the plates.

13. A clamping assembly as claimed in claim 12, wherein the horizontal portion of the "L" of each plate is triangular in shape with the rear section of each plate being the base and the front section being the apex of the triangle.

14. A clamping assembly as claimed in claim 12 wherein the vertical "L" portion of each plate is a post extending from the bottom surface of the horizontal "L" portion; and wherein said means for securing the first plate to a first bone section and the second plate to a second bone section includes, for each plate, a spike midway along the post, extending from said post in a direction generally parallel to the horizontal portion of the "L" of each plate.

15. A clamping assembly as claimed in claim 14 wherein said post of each plate extends along the side surface of its respective bone section for a length approximately equal to the thickness of the bone section, and wherein said post includes an obliquely formed hole in the bottom portion of the post.

16. A clamping assembly as claimed in claim 15 wherein each horizontal "L" portion includes a notch at the center of its rear portion to guide a second, circumferential wire.

17. A clamping assembly as claimed in claim 16 wherein said second wire is positioned underneath the bone sections and through the oblique holes.

18. A clamping assembly as claimed in claim 16 wherein each vertical "L" section defines a post and each post includes a recessed pressure point on the side of the post opposite the side on which the spike is mounted for enabling compression means to be applied to that pressure point to push the spike into its associated bone section.

19. A clamping assembly for clamping together first and second sections of bone having, when so clamped, a common external surface generally perpendicular to contacting surfaces of the first and second bone sections, and each bone section having a side surface generally parallel to said common contacting surfaces and transversely joined to said common external surface, the clamping assembly comprising:

first and second plates, each plate having a flat top section, with the top section of the first plate being disposed on the first bone section and the top section of the second plate being disposed on the second bone section, each flat top section having a predetermined thickness between top and bottom surfaces and with a groove formed between the top and bottom surfaces for enabling a wire to pass within the groove between the top and bottom surfaces; each plate also having a side post secured to its flat top section and means for securing the plate to its respective section of bone; and a wire passing along the back of each plate and along a grooved portion of each flat top section in a figure-of-8 configuration for pulling said plates toward each other and for compressing the two bone sections together without the figure-of-8 wire touching the bone sections.

20. A clamping assembly as claimed in claim 19 wherein said means for securing the plate includes a spike connected midway along the length of the side post for insertion into the side surface of the bone section and thereby securing the plate to the bone section.

21. A clamping assembly as claimed in claim 19 wherein, as to each plate, said side post has a top and a bottom end and wherein it is secured at its top end to a flat bottom and at its bottom end to a flat bottom section intended to be disposed underneath a respective bone section for securing the plate to the bone section.

22. A method for clamping together first and second sections of bone having, when so clamped, a common external surface generally perpendicular to contacting surfaces of the first and second bone sections, and each bone section having a side surface generally parallel to said contacting surfaces and transversely joined to said common external surface, comprising the steps of:

disposing first and second plates to respective first and second bone sections in general alignment opposite each other, where each plate includes a horizontal section connected to a vertical section, and where the horizontal section of each plate has a top surface and a bottom surface with a groove therebetween for enabling a first wire to pass through the groove between the top and bottom surfaces;

securing the first plate to the first bone section and the second plate to the second bone section, with the horizontal portion of each plate resting on the common external surface and the vertical portion of each plate abutting the corresponding side surface of the bone section; and positioning a first wire within at least a portion of said groove and winding the wire between the first and second plates for pulling the two plates toward each other and simultaneously compressing the two bone sections together without the wire touching the bone surface underneath the plate and without the wire extending above the top surface of the plates.

23. A method as claimed in claim 22 wherein each vertical section includes an oblique hole and wherein the method includes passing a second, circumferential, wire beneath the bone sections through the oblique holes and around the plates and then twisting together the ends of the second wire to hold and compress the bone sections.

* * * * *